(12) United States Patent
Takahashi

(10) Patent No.: US 10,416,121 B2
(45) Date of Patent: Sep. 17, 2019

(54) COMPOSITE MATERIAL MOLDING JIG, COMPOSITE MATERIAL MOLDING METHOD, ULTRASONIC TEST SYSTEM, ULTRASONIC TEST METHOD AND AIRCRAFT STRUCTURAL OBJECT

(71) Applicant: FUJI JUKOGYO KABUSHIKI KAISHA, Tokyo (JP)

(72) Inventor: Kohei Takahashi, Tokyo (JP)

(73) Assignee: SUBARU CORPORATION, Tokyo (JP)

( * ) Notice: Subject to any disclaimer, the term of this patent is extended or adjusted under 35 U.S.C. 154(b) by 93 days.

(21) Appl. No.: 15/451,792

(22) Filed: Mar. 7, 2017

(65) Prior Publication Data

US 2017/0276648 A1 Sep. 28, 2017

(30) Foreign Application Priority Data

Mar. 24, 2016 (JP) .................................. 2016-60990

(51) Int. Cl.
*B29C 59/02* (2006.01)
*B29C 65/48* (2006.01)
(Continued)

(52) U.S. Cl.
CPC ......... *G01N 29/2418* (2013.01); *B29C 43/58* (2013.01); *B29C 59/022* (2013.01);
(Continued)

(58) Field of Classification Search
CPC . B29C 59/022; B29C 65/4855; B29C 59/026; B29C 70/34; B29C 70/42;
(Continued)

(56) References Cited

U.S. PATENT DOCUMENTS 4,869,770 A 9/1989 Christensen et al.
5,397,415 A * 3/1995 Manabe .................. B26D 3/08
156/234

(Continued)

FOREIGN PATENT DOCUMENTS

CN 1946530 A 4/2007
JP S62-193821 A 8/1987
(Continued)

OTHER PUBLICATIONS

Extended European Search Report dated Jan. 4, 2018 in EP Patent Application No. 17 155 243.3 (12 pages).
(Continued)

*Primary Examiner* — Jacques M Saint Surin
(74) *Attorney, Agent, or Firm* — Smith, Gambrell & Russell, LLP

(57) ABSTRACT

According to one implementation, a composite material molding jig includes a rigid portion and a convex portion for forming a groove for inserting an optical fiber sensor. The rigid portion has a surface for laminating prepreg sheets. The convex portion is formed in a surface side of the rigid portion. Further, according to one implementation, a composite material molding method is a method for molding a composite material, on which the groove for inserting the optical fiber sensor has been formed, by heating and curing a laminated body of the prepreg sheets laminated on the above-mentioned composite material molding jig.

11 Claims, 11 Drawing Sheets

(51) Int. Cl.
| | |
|---|---|
| *B32B 5/10* | (2006.01) |
| *B32B 7/12* | (2006.01) |
| *B32B 27/00* | (2006.01) |
| *B32B 37/12* | (2006.01) |
| *B64C 3/18* | (2006.01) |
| *G01N 29/04* | (2006.01) |
| *B29C 70/34* | (2006.01) |
| *B29C 70/42* | (2006.01) |
| *B29C 43/58* | (2006.01) |
| *G01N 29/24* | (2006.01) |
| *B29L 31/30* | (2006.01) |
| *B29C 33/42* | (2006.01) |
| *B29C 43/02* | (2006.01) |
| *B29K 105/06* | (2006.01) |
| *B29C 33/00* | (2006.01) |

(52) U.S. Cl.
CPC ........ *B29C 59/026* (2013.01); *B29C 65/4855* (2013.01); *B29C 70/34* (2013.01); *B29C 70/42* (2013.01); *B32B 5/10* (2013.01); *B32B 7/12* (2013.01); *B32B 27/00* (2013.01); *B32B 37/12* (2013.01); *B64C 3/18* (2013.01); *G01N 29/043* (2013.01); *B29C 33/42* (2013.01); *B29C 43/021* (2013.01); *B29C 2033/0094* (2013.01); *B29C 2043/5808* (2013.01); *B29K 2105/06* (2013.01); *B29K 2995/0001* (2013.01); *B29L 2031/3076* (2013.01); *B29L 2031/3082* (2013.01); *B32B 2307/10* (2013.01); *B32B 2605/18* (2013.01); *Y02T 50/43* (2013.01)

(58) Field of Classification Search
CPC ....... B29C 43/58; B29C 33/42; B29C 43/021; B29C 2033/0094; B29C 2043/5808; B64C 3/18; B32B 37/12; B32B 7/12; B32B 5/10; B32B 27/00; B32B 2605/18; B32B 2307/10; G01N 29/2418; G01N 29/043; Y02T 50/43; B29L 2031/3076; B29L 2031/3082; B29K 2995/0001; B29K 2105/06
USPC .......................................................... 73/655
See application file for complete search history.

(56) References Cited

U.S. PATENT DOCUMENTS

| | | | |
|---|---|---|---|
| 6,759,002 B1* | 7/2004 | Engwall | B23Q 3/086 156/245 |
| 7,017,421 B2 | 3/2006 | Kehlenbach | |
| 9,180,653 B2 | 11/2015 | Minamida et al. | |
| 2004/0188882 A1* | 9/2004 | Matsumoto | B29C 70/446 264/257 |
| 2006/0019088 A1 | 1/2006 | Wang et al. | |
| 2009/0008529 A1 | 1/2009 | Sugimoto et al. | |
| 2013/0189430 A1* | 7/2013 | Shimizu | B29C 70/086 427/243 |

FOREIGN PATENT DOCUMENTS

| | | |
|---|---|---|
| JP | H02-139209 A | 5/1990 |
| JP | H05-164755 A | 6/1993 |
| JP | H11-142262 | 5/1999 |
| JP | 2004-004030 A | 1/2004 |
| JP | 2005-134189 A | 5/2005 |
| JP | 2012-006337 A | 1/2012 |
| JP | 2012-020483 | 2/2012 |
| JP | 5424203 | 2/2014 |
| JP | 2014-52368 A | 3/2014 |
| WO | 97/19325 A1 | 5/1997 |
| WO | 2005/097449 A2 | 10/2005 |
| WO | 2008-123285 A1 | 10/2006 |
| WO | 2013/061682 | 5/2013 |
| WO | 2015/132700 A1 | 9/2015 |

OTHER PUBLICATIONS

Partial European Search Report dated Sep. 20, 2017 in Patent Application No. 17 155 243.3 (15 pages).
Japanese Office Action dated Oct. 3, 2017 for JP 2016-060990 (9 pages—Japanese and English translation).
First Chinese Office Action dated Oct. 26, 2018 in CN Patent Application No. 201710095777.4 (6 pages in Chinese with English Translation).
Chinese Search Report dated Oct. 18, 2018 in CN Patent Application No. 201710095777.4 (2 page).
Second Chinese Office Action dated Apr. 25, 2019 in CN Patent Application No. 201710095777.4 (4 pages in Chinese with English Translation).

* cited by examiner

COMPOSITE MATERIAL MOLDING JIG, COMPOSITE MATERIAL MOLDING METHOD, ULTRASONIC TEST SYSTEM, ULTRASONIC TEST METHOD AND AIRCRAFT STRUCTURAL OBJECT

CROSS REFERENCES TO RELATED APPLICATIONS

This application is based upon and claims the benefit of priority from Japanese Patent Application No. 2016-060990, filed on Mar. 24, 2016; the entire contents of which are incorporated herein by reference.

FIELD

Implementations described herein relate generally to a composite material molding jig, a composite material molding method, an ultrasonic test system, an ultrasonic test method and an aircraft structural object.

BACKGROUND

Conventionally, ultrasonography is known as a method of nondestructively testing a structural member of an aircraft or the like. Furthermore, a technique using an FBG (fiber Bragg grating) sensor as a sensor for ultrasonic testing is also known. Using an FBG sensor as a sensor for receiving an ultrasonic wave can improve detection accuracy of ultrasonic waves compared to a case where an ultrasonic transducer is used as the sensor.

Thus, a technique of forming a groove on a metallic substrate by pressing a bar-shaped member against the metallic substrate so that an optical fiber sensor can be inserted into the metal groove has been proposed (for example, refer to International Publication No. WO 2008/123285 A1). With this technique, an optical fiber sensor can be embedded between metals joined by hot pressing.

On the other hand, a composite material, such as GFRP (glass fiber reinforced plastics) or CFRP (carbon fiber reinforced plastics), which is lightweight and has high strengths, has attracted attention mainly as a material of an aircraft structural object or the like. A composite material is manufactured by laminating and curing semi-cured sheet-like prepregs, each of which made of fibers, such as carbon fibers or glass fibers, impregnated with resin.

Thus, a technique of embedding an optical fiber, as a strain sensor, between sheet-like prepregs, which are a material before curing of a composite material, and then, curing the prepregs between which the optical fiber is embedded has been proposed (for example, refer to Japanese Patent Application Publication JP 2012-020483 A and Japanese Patent Application Publication JP H11-142262 A). Specifically, a composite material, in which an optical fiber has been embedded, can be manufactured by inserting the optical fiber between prepreg sheets during laminating the prepregs, precedential to curing the prepreg sheets.

However, the thickness of a typical optical fiber sensor is 100 μm order, thereby rigidity is low. Accordingly, when an optical fiber is inserted between prepreg sheets before curing, there is a problem that the optical fiber moves from an appropriate position by shrinkage of a composite material due to the curing.

Thus, an object of the present invention is to allow embedding an optical fiber sensor at an appropriate position, without deteriorating strength of a composite material.

SUMMARY OF THE INVENTION

In general, according to one implementation, a composite material molding jig includes a rigid portion and a convex portion for forming a groove for inserting an optical fiber sensor. The rigid portion has a surface for laminating prepreg sheets. The convex portion is formed in a surface side of the rigid portion.

Further, according to one implementation, a composite material molding method is a method for molding a composite material, on which the groove for inserting the optical fiber sensor has been formed, by heating and curing a laminated body of the prepreg sheets laminated on the above-mentioned composite material molding jig.

Further, according to one implementation, a composite material molding method includes: producing a laminated body of prepregs, which has a groove for inserting an optical fiber sensor; and molding a composite material, having the groove, by curing the laminated body of the prepregs. The groove is formed without cutting fibers of the prepregs. A length direction of the groove is a length direction of the fibers.

Further, according to one implementation, an ultrasonic test system includes an ultrasonic transducer, an optical fiber sensor and a signal processing system. The ultrasonic transducer emits an ultrasonic wave. The optical fiber sensor detects at least one of the ultrasonic wave having transmitted a test area of an object to be tested made of a composite material and a reflected wave of the ultrasonic wave having reflected in the test area, and outputs a detection signal. The signal processing system detects a defect in the test area based on the detection signal output from the optical fiber sensor. The optical fiber sensor is inserted into a groove formed between uncut fibers of the composite material.

Further, according to one implementation, an ultrasonic test method includes: molding a composite material having a groove by curing a laminated body of prepregs having the groove; inserting an optical fiber sensor into the groove of the composite material; and performing an ultrasonic test of the composite material using the optical fiber sensor.

Further, according to one implementation, an aircraft structural object includes the above-mentioned ultrasonic test system as a part.

BRIEF DESCRIPTION OF THE DRAWINGS

In the accompanying drawings:

FIG. 15 is a sectional view of the composite material molding jig at the position A-A in FIG. 14;

DETAILED DESCRIPTION

A composite material molding jig, a composite material molding method, an ultrasonic test system, an ultrasonic test method and an aircraft structural object according to implementations of the present invention will be described with reference to the accompanying drawings.

(First Implementation)
(Structure of Composite Material Molding Jig)

Figure 1:
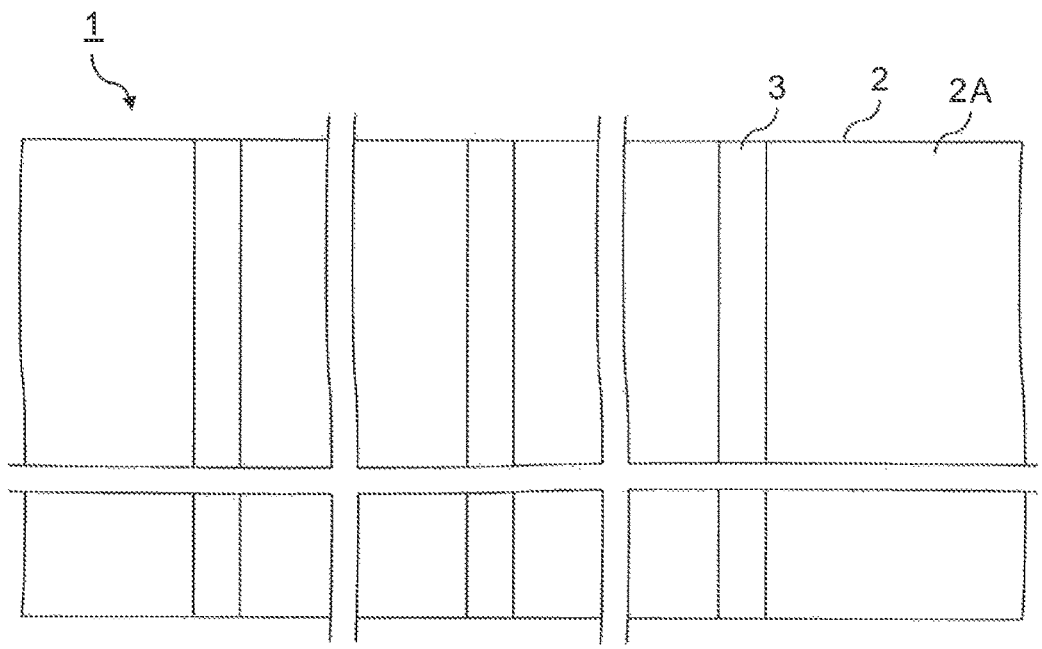
FIG. 1 is a top view showing a structure of a composite material molding jig according to the first implementation of the present invention.
Figure 2:
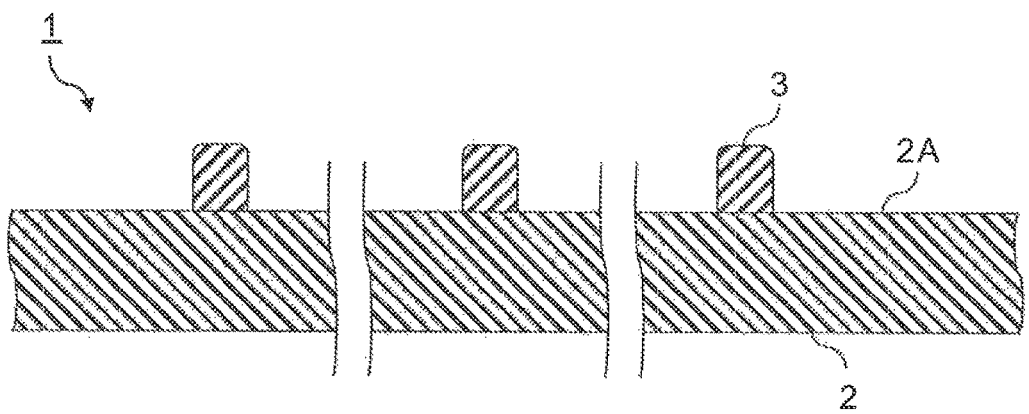
FIG. 2 is a sectional view of the composite material molding jig shown in FIG. 1.

FIG. 1 is a top view showing a structure of a composite material molding jig according to the first implementation of the present invention. FIG. 2 is a sectional view of the composite material molding jig shown in FIG. 1.

A composite material molding jig 1 is a jig for manufacturing a composite material to which an optical fiber sensor has been attached as a sensor for detecting an ultrasonic wave. The composite material molding jig 1 has a rigid portion 2 and at least one convex portion 3 formed on the rigid portion 2. The rigid portion 2 has a surface 2A for laminating prepreg sheets. Each convex portion 3 is used for forming a groove, which is for inserting an optical fiber sensor, on a laminated body of prepreg sheets. Therefore, each convex portion 3 is formed in the surface 2A side of the rigid portion 2 and has an elongated structure corresponding to a shape of the groove.

In the case of forming a plurality of grooves on a laminated body of prepreg sheets so that a plurality of optical fiber sensors can be inserted, a plurality of the convex portions 3 can be formed on the rigid portion 2, according to the number of the grooves, as shown in the figures. In this case, the convex portions 3 are formed so that the length directions of the convex portions 3 become uniform. Therefore, the length directions of the convex portions 3 become approximately parallel.

Figure 3:
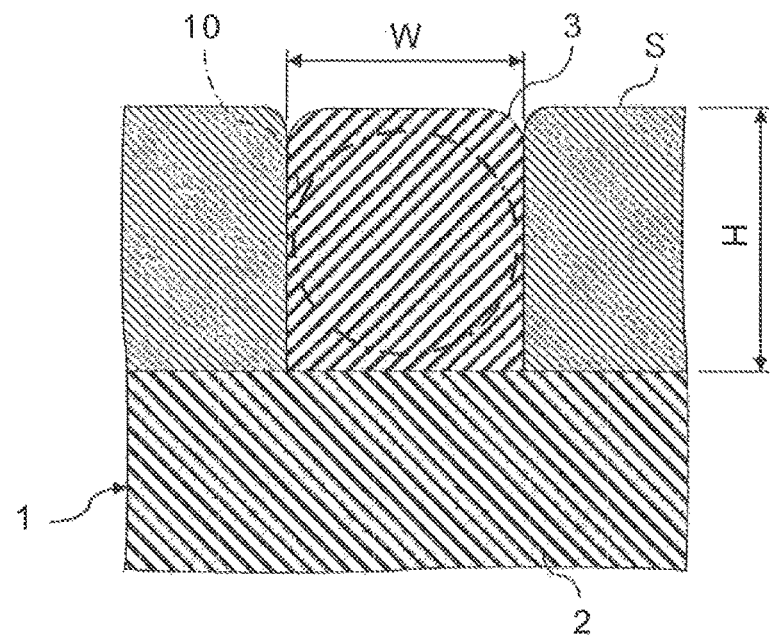
FIG. 3 is an enlarged cross-sectional view of each convex portion shown in FIG. 1 and FIG. 2, which illustrates a method of determining the height and the width of the convex portion.

FIG. 3 is an enlarged cross-sectional view of each convex portion 3 shown in FIG. 1 and FIG. 2, which illustrates a method of determining the height and the width of the convex portion 3.

What is necessary in order to form a groove, which has a size capable of housing an optical fiber sensor 10, on a laminated body of prepregs is to make the height H of the convex portion 3 and the width W of the cross section of the convex portion 3 be a height and a width according to the diameter of the optical fiber sensor 10 respectively as shown in FIG. 3. That is, what is necessary is to make the height H and the width W of the convex portion 3 be a height and a width each obtained by adding a necessary allowance to the diameter of the optical fiber sensor 10.

The diameter of the typical optical fiber sensor 10 is about from 125 μm to 150 μm. Therefore, what is necessary in order to form a groove, which has a size capable of housing the typical optical fiber sensor 10, on a laminated body of prepregs is to make the height H of each convex portion 3 and the width W of the cross section of each convex portion 3 be not less than 125 μm and not more than 150 μm, respectively.

The thickness of a typical prepreg sheet S laminated on the surface 2A of the rigid portion 2 is also about from 125 μm to 150 μm. Therefore, when the diameter of the optical fiber sensor 10 and the thickness of the prepreg sheet S are nearly equal to each other, the height H of each convex portion 3 can be a height of one ply of the prepreg sheet S. In this case, a groove which has a depth corresponding to the thickness of one ply of the prepreg sheet S is to be formed on a laminated body of prepregs.

An allowable range in the thickness of the prepreg sheet S may be determined by design information in order to obtain necessary mechanical characteristics, such as strengths of a composite material. Furthermore, the thickness of the easily available prepreg sheet S, which is supplied by manufacturers of a prepreg, is often limited. Meanwhile, the diameter of the optical fiber sensor 10 has high flexibility in selection. Thus, the diameter of the optical fiber sensor 10 can be determined according to the thickness of the prepreg sheet S, and the height H of each convex portion 3 and the width W of the cross section of each convex portion 3 can be determined according to the thickness of the prepreg sheet S and the diameter of the optical fiber sensor 10.

As a matter of course, in the case of forming a groove for inserting the optical fiber sensor 10, which has a diameter nearly equal to the thickness of some plies of the sheets S of prepregs, on a laminated body of prepregs, the height H of each convex portion 3 can be made nearly equal to the thickness of the plies of the sheets S of prepregs according to the diameter of the optical fiber sensor 10.

Note that, the thickness of the prepreg sheet S and the diameter of the optical fiber sensor 10 also tend to become small with progress in technology. Therefore, the height H of each convex portion 3 and the width W of the cross section of each convex portion 3 may also be less than 125 μm, respectively, depending on the thickness of the prepreg sheet S and the diameter of the optical fiber sensor 10.

(Composite Material Molding Method)

Next, a molding method of a composite material using the composite material molding jig 1 will be described. A composite material on which grooves for inserting the optical fiber sensors 10 have been formed can be molded by heating and curing a laminated body prepregs on the composite material molding jig 1 which has a structure as shown in FIG. 1. Furthermore, a composite material integrated with the optical fiber sensors 10 can be produced by inserting the optical fiber sensors 10 into the composite material on which the grooves have been formed.

Figure 4:
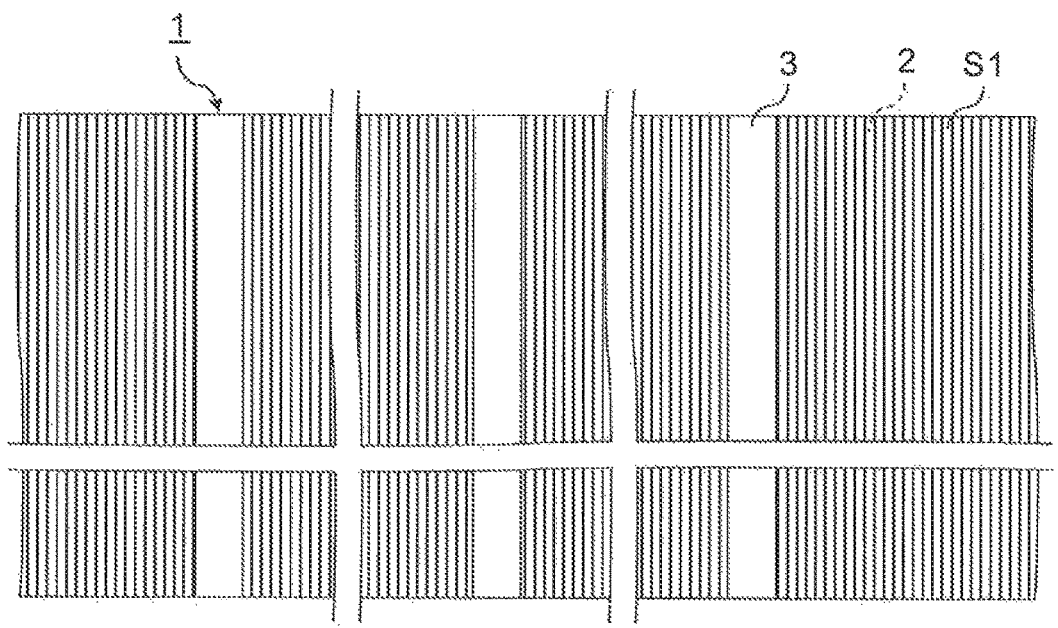
FIG. 4 is a top view showing a state where one ply of prepreg sheet has been disposed on the composite material molding jig shown in FIG. 1.
Figure 5:
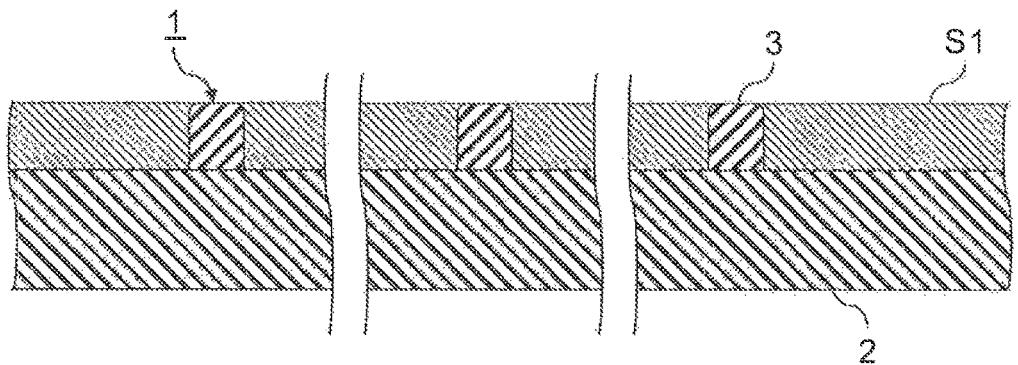
FIG. 5 is a sectional view of the composite material molding jig and the prepreg sheet shown in FIG. 4.

FIG. 4 is a top view showing a state where one ply of prepreg sheet S1 has been disposed on the composite material molding jig 1 shown in FIG. 1. FIG. 5 is a sectional view of the composite material molding jig 1 and the prepreg sheet S1 shown in FIG. 4.

As shown in FIG. 4 and FIG. 5, the first ply of the prepreg sheet S1 can be laminated in each of both sides of each convex portion 3, respectively, with setting the length direction of fibers to be the length direction of the convex portions 3. Therefore, the prepreg sheet S1 in which the length direction of fibers is one direction is used as the first ply. For example, the prepreg sheet S1 can be laminated in both sides of each convex portion 3 with spreading the prepreg sheet S1 by hand or an instrument. Alternatively, a plurality of prepreg sheets S1 which have previously been cut may be disposed in both sides of each convex portion 3.

In the case of inserting a plurality of the optical fiber sensors 10 into a composite material, intervals of the optical fiber sensors 10 can be determined depending on sensitivity of the optical fiber sensors 10 so that a necessary detection area can be tested. As a specific example, the optical fiber sensors 10 can be disposed in parallel at intervals of about 0.5 m. In that case, intervals of the convex portions 3 are made to be the intervals of the optical fiber sensors 10.

When the parallel convex portions 3 have been formed on the rigid portion 2, the prepreg sheet S1 which has previously been cut according to an interval of the adjacent convex portions 3 can be laminated between the adjacent convex portions 3. In other words, the prepreg sheet S1 which has a width same as an interval of the adjacent convex portions 3 can be prepared and laminated between the adjacent convex portions 3.

When the height of the convex portions 3 has been determined to be the thickness of plural plies of the prepreg sheets S1, the plies of the prepreg sheets S1 are to be laminated in each of both sides of each convex portion 3 respectively so that the length direction of fibers becomes the length direction of the convex portions 3. In this case, each of the plies of the prepreg sheets S1 is laminated in the same direction so that the length direction of fibers coincides with the length direction of the convex portions 3. Hereinafter, an example case where the height of the convex portions 3 has been determined to be the thickness of one ply of the prepreg sheet S1, as shown in the figures, will be described.

Figure 6:
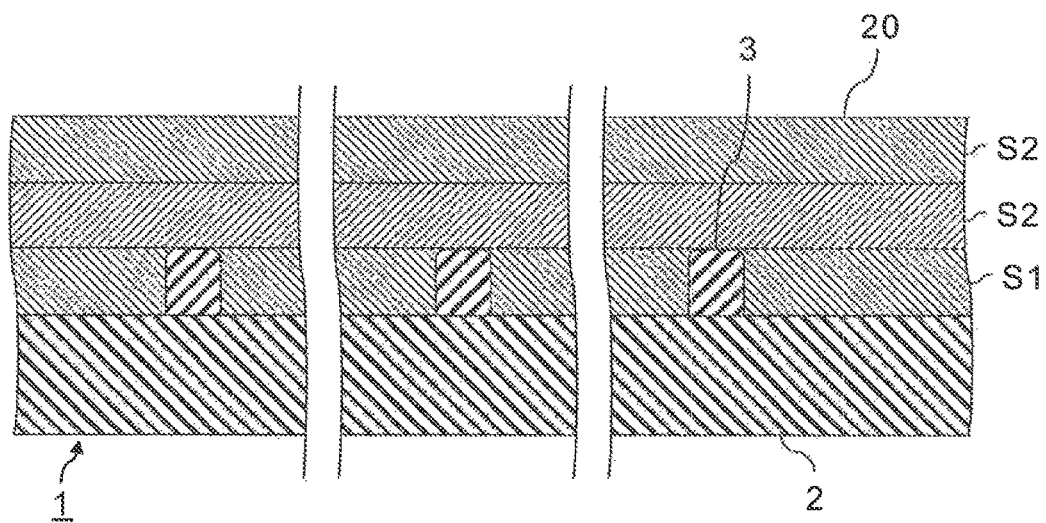
FIG. 6 is a sectional view showing a state where the second and following plies of prepreg sheets have been laminated on the first ply of the prepreg sheet S1 shown in FIG. 5.

FIG. 6 is a sectional view showing a state where the second and following plies of prepreg sheets S2 have been laminated on the first ply of the prepreg sheet S1 shown in FIG. 5.

Since the height of the convex portions 3 is determined to be the thickness of the prepreg sheets S1, an approximately plane is formed by the top surfaces of the convex portions 3 and the surfaces of the first ply of the prepreg sheets S1 when the prepreg sheets S1 are disposed in both sides of each convex portion 3. Therefore, the second and following plies of the prepreg sheets S2 can be laminated in a usual lamination method. Thereby, the second and following plies of the prepreg sheets S2 may be laminated automatically using a laminating device.

The fibers of the second and following plies of the prepreg sheets S2, which are laminated above the top surfaces of the convex portions 3, can be directed to desired directions. Therefore, in order to laminate the prepreg sheets S2, which are laminated above the top surfaces of the convex portions 3, a preferable lamination method, such as one way, pseudo isotropic, or cross ply can be selected.

When a direction of at least a part of fibers of the prepreg sheets S2, which are laminated above the top surfaces of the convex portions 3, is determined so that the length direction of the fibers intersects with the longitudinal direction of the convex portions 3 at a perpendicular or predetermined angle, strengths of a composite material in the direction perpendicular to the longitudinal direction of the convex portions 3 can be secured. Therefore, it is appropriate to make the length direction of the fibers of the prepreg sheet S1, which is laminated below the top surfaces of the convex portions 3, be the longitudinal direction of the convex portions 3 while it is appropriate to make a direction of at least a part of fibers of the prepreg sheets S2, which are laminated above the top surfaces of the convex portions 3, be a direction intersecting with the longitudinal direction of the convex portions 3, from a viewpoint of sufficiently securing strengths of a composite material after thermal curing.

As exemplified in FIG. 6, when the necessary number of the prepreg sheets S2 to secure the thickness of a composite material are laminated above the top surfaces of the convex portions 3, grooves which have shapes same as those of the convex portions 3 are formed, on a laminated body 20 of the prepreg sheets S. That is, the laminated body 20 of prepregs, which has the grooves for inserting the optical fiber sensors 10, can be manufactured.

When the laminated body 20 of prepregs, having the grooves, laminated on the composite material molding jig 1 is heated and cured, in a pressurized state, by an autoclave processing equipment or the like, a composite material which has the grooves for inserting the optical fiber sensors 10 can be molded. As a pressurization method of the laminated body 20, a method of covering the laminated body 20 of prepregs with a bagging film and decompressing a region inside the bagging film to make the region inside the bagging film be a vacuum state, or a method of pressurizing the laminated body 20 by pressing a rigid jig, which is called mandrel, against the laminated body 20 is typical.

The composite material molding jig 1 may be used only as a jig for laminating prepregs while the laminated body 20 of prepregs may be heated and cured using another jig for thermal curing. When the composite material molding jig 1 is also used as a jig for heating and curing the laminated body 20, grooves formed on a composite material in order to insert the optical fiber sensors 10 can have shapes exactly same as those of the convex portions 3.

As described above, when the laminated body 20 of prepregs is heated and cured after forming grooves on the laminated body 20 so that the length direction of the grooves becomes the length direction of fibers of prepregs, the grooves can be formed on the laminated body 20 of prepregs and a composite material without, cutting the fibers.

Figure 7:
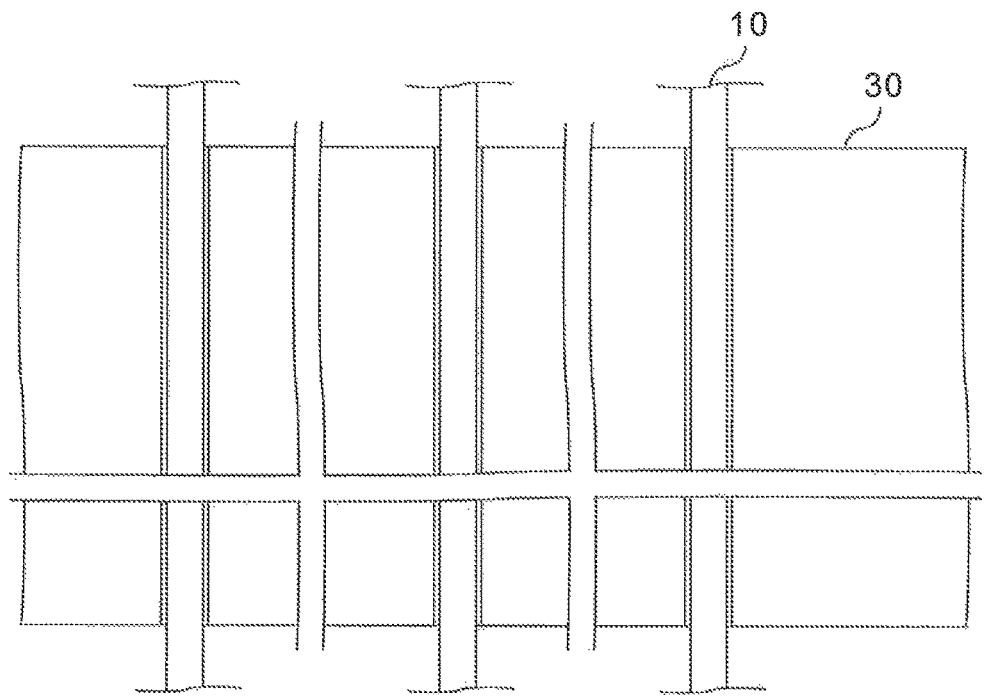
FIG. 7 is a top view showing a state where the optical fiber sensors have been inserted into grooves of a composite material molded by heating and curing the laminated body of prepregs shown in FIG. 6.

FIG. 7 is a top view showing a state where the optical fiber sensors 10 have been inserted into grooves of a composite material 30 molded by heating and curing the laminated body 20 of prepregs shown in FIG. 6.

When the composite material 30 after the thermal curing is detached from the composite material molding jig 1, grooves which have cross-sectional shapes similar to the cross-sectional shapes of the convex portions 3 are formed on the surface of the composite material 30 in the composite material molding jig 1 side. That is, grooves can be processed on the composite material 30 by forming the laminated body 20 of prepregs under heating and pressurization, without processing using plastic deformation of a material, such as cutting processing or bending processing.

The grooves of the composite material 30 are used to insert the optical fiber sensors 10. Specifically, as exemplified in FIG. 7, the optical fiber sensors 10 are inserted into the grooves formed on the composite material 30. At this time, an adhesive is applied between the optical fiber sensors 10 and the grooves. The adhesive may be applied to either the optical fiber sensors 10 or the inner faces of the grooves, or both of the optical fiber sensors 10 and the inner faces of the grooves. Furthermore, the adhesive may be applied before inserting the optical fiber sensors 10 into the grooves, or after inserting the optical fiber sensors 10 into the grooves.

Figure 8:
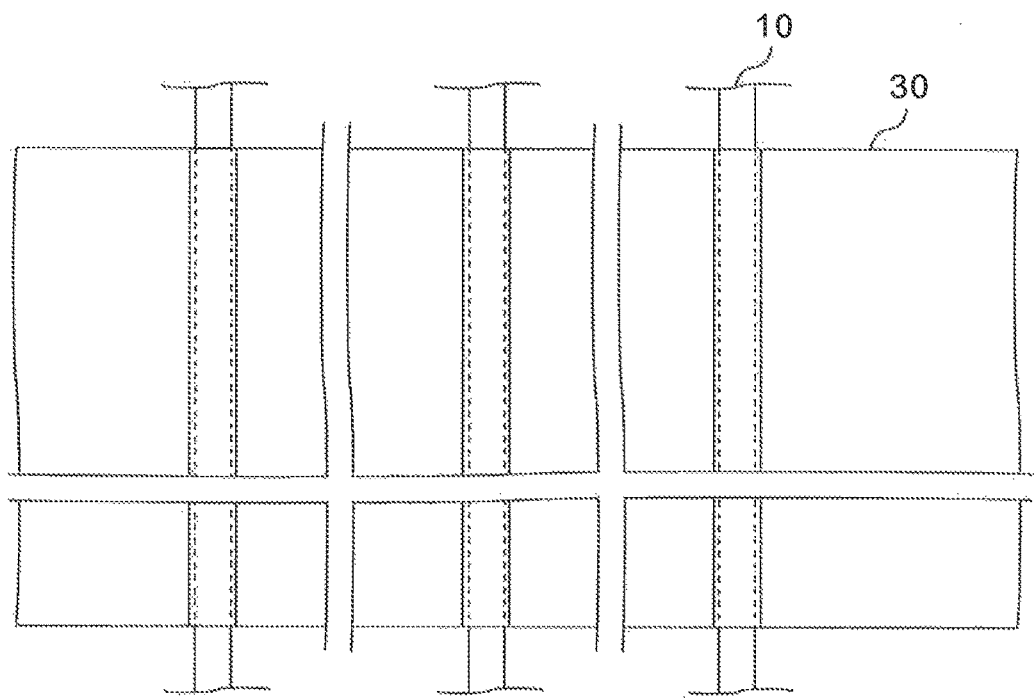
FIG. 8 is a top view showing a state where an adhesive for fixing the optical fiber sensors, shown in FIG. 7, to the composite material has been hardened.

FIG. 8 is a top view showing a state where an adhesive for fixing the optical fiber sensors 10, shown in FIG. 7, to the composite material 30 has been hardened.

When the adhesive for fixing the optical fiber sensors 10 to the composite material 30 is hardened, the composite material 30 integrated with the optical fiber sensors 10 can be produced as exemplified in FIG. 8. When the composite material 30 is used as a part of an aircraft structural object, a thermosetting resin is usually used as the adhesive. In that case, the composite material 30 integrated with the optical fiber sensors 10 is produced by thermal curing of the adhesive by a heating device.

The above-mentioned composite material 30 in which the optical fiber sensors 10 have been embedded in the surface can be used as a desired part, such as an aircraft part. In the above-mentioned example, the surface of the composite material 30 in the side where the optical fiber sensors 10 are to be embedded is flat. As a matter of course, the surface of the composite material 30 in the side where the optical fiber sensors 10 are to be embedded may also be a curved surface depending on an intended purpose of the composite material 30. In the case of curving the surface of the composite material 30, the surface of the composite material 30 can be curved both in the length direction of the optical fiber sensors 10 and in the direction perpendicular to the length direction of the optical fiber sensors 10. Therefore, the composite material 30 in which the optical fiber sensors 10 have been embedded can be produced not only for a panel, which is a part of a wing structural object of an aircraft, but also for a reinforcement member, such as a spar, a rib, or a stringer.

Figure 9:
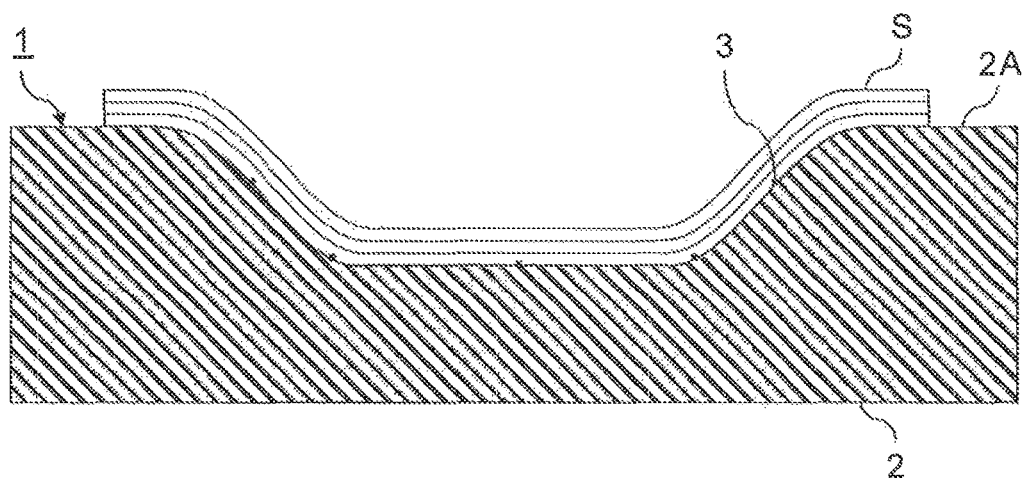
FIG. 9 shows a method of manufacturing the composite material in the case of curving a part of the surface of the composite material, in which the optical fiber sensors are embedded.

FIG. 9 shows a method of manufacturing the composite material 30 in the case of curving a part of the surface of the composite material 30, in which the optical fiber sensors 10 are embedded.

In the case of curving the surface of the composite material 30, what is necessary is to curve the surface 2A of the rigid portion 2 of the composite material molding jig 1, for laminating the prepreg sheets S, according to the shape of the composite material 30 after curing, as exemplified in FIG. 9. The convex portions 3 for forming the grooves for inserting the optical fiber sensors 10 can also be formed on the curved surface 2A. Thereby, even when the surface of the composite material 30 is a curved surface, the optical fiber sensors 10 can be fixed to the composite material 30 at predetermined intervals.

As described above, the molding method of the composite material 30 is to form the convex portions 3 for forming grooves on the composite material molding jig 1 for laminating the prepreg sheets 5, to insert the optical fiber sensors 10 into the grooves formed on the composite material 30 after curing, and to fix the optical fiber sensors 10 to the composite material 30 with an adhesive. Furthermore, the prepreg sheets S1 each laminated at a position lower than each of the top surfaces of the convex portions 3 is disposed so that the length direction of the fibers of the prepreg sheets S1 becomes the length direction of the convex portions 3.

(Effects)

Thus, the molding method of the composite material 30 using the composite material molding jig 1 allows manufacturing the high-quality composite material 30 of which the optical fiber sensors 10 have been embedded in the surface. In other words, the optical fiber sensors 10 can be embedded at appropriate positions on the surface without deteriorating strengths of the composite material 30.

Figure 10A:
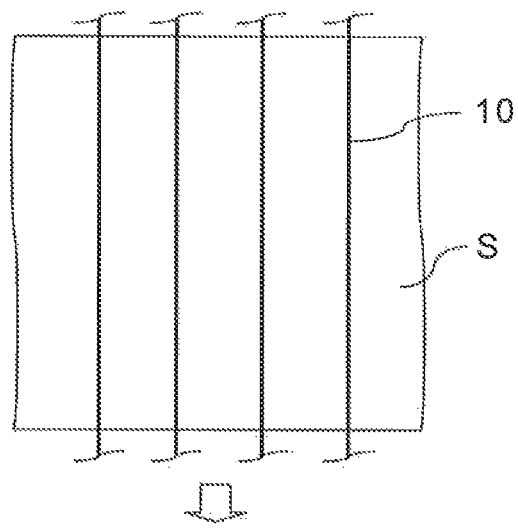
FIGS. 10A-10C explain problems of the conventional molding method of a composite material, which places the optical fiber sensors between the prepreg sheets and subsequently cures the prepreg sheets.
Figure 10B:
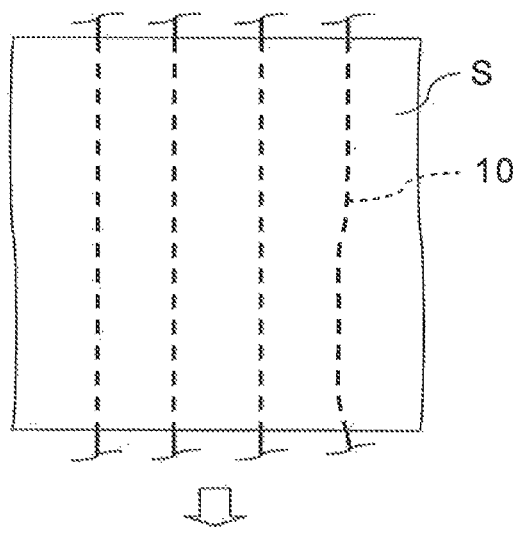
Figure 10C:
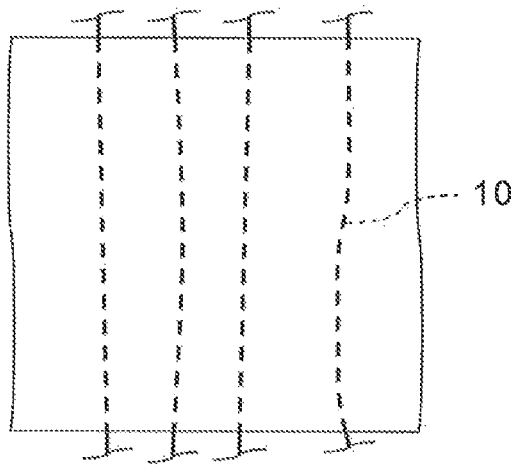

FIGS. 10A-10C explain problems of the conventional molding method of a composite material, which places the optical fiber sensors 10 between the prepreg sheets S and subsequently cures the prepreg sheets S.

Even when the optical fiber sensors 10 have been arrayed on a certain prepreg sheet S as shown in FIG. 10A, the atmospheric pressure is applied on the optical fiber sensors 10 by vacuuming at the time of curing the prepregs, in addition to own weight of the prepreg sheets S laminated on the optical fiber sensors 10. Accordingly, the optical fiber sensors 10 each having a low rigidity may move from the initial positions as shown in FIG. 10B. Furthermore, when the laminated prepregs are heated and cured, the positions of the optical fiber sensors 10 are further changed by shrinkage due to the curing as shown in FIG. 10C.

By contrast, in the molding method of the composite material 30 using the composite material molding jig 1 as described above, the optical fiber sensors 10 are inserted into the grooves of the cured composite material 30. Therefore, displacement of the optical fiber sensors 10 can be avoided, and the optical fiber sensors 10 can be stably and easily embedded at appropriate positions on a surface of the composite material 30.

Figure 11:
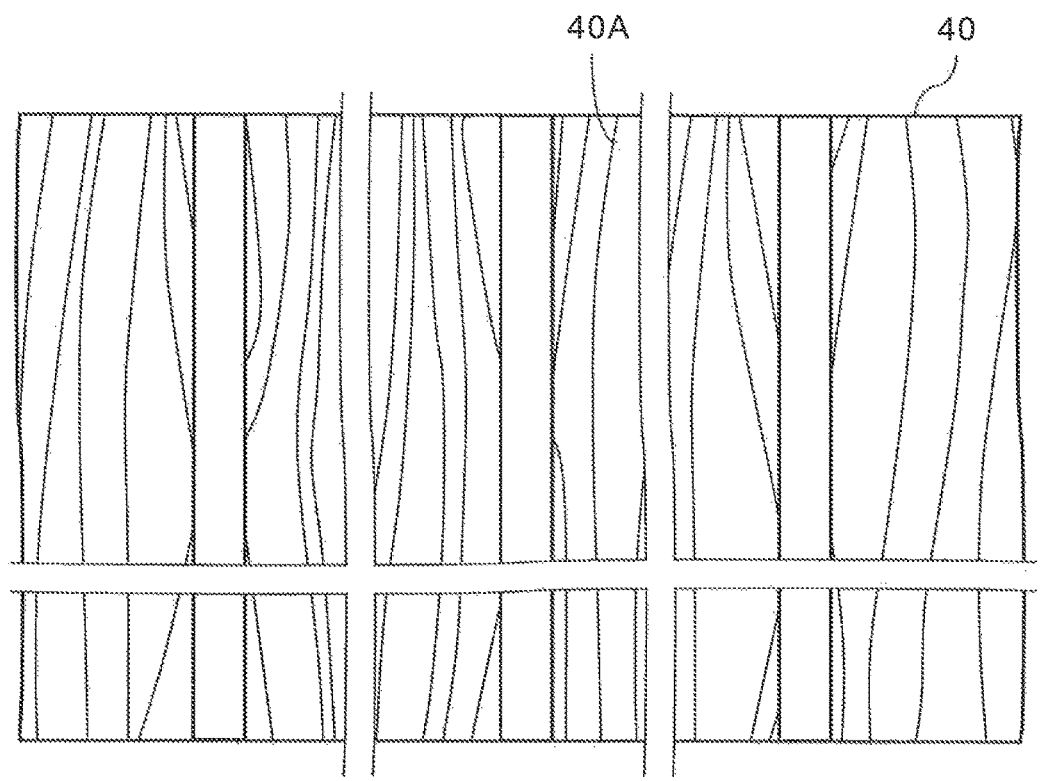
FIG. 11 explains problems in the case of processing grooves, for placing the optical fiber sensors, on the composite material after curing.

FIG. 11 explains problems in the case of processing grooves, for placing the optical fiber sensors 10, on the composite material 40 after curing.

It is also considered to form grooves, for placing the optical fiber sensors 10, on a composite material 40 after curing by cutting processing or press processing. However, fibers 40A of the composite material 40 after curing are not necessarily linear unlike fibers woven into prepregs, as exemplified in FIG. 11. That is, undulation occurs in the fibers 40A of the composite material 40. This is because displacement of prepregs occurs at the time of laminating prepreg sheets and bagging, and deformation of the prepregs occurs at the time of curing.

Therefore, on the condition that grooves are formed, by machining, on the composite material 40 after curing, a large number of the complexly tangled fibers 40A are to be cut as exemplified in FIG. 11. Alternatively, a large number of the fibers 40A are damaged. Accordingly, it leads to deterioration in strengths of the composite material 40.

By contrast, the optical fiber sensors 10 integrated with the composite material 30 are disposed in the grooves formed without cutting processing or press processing of the composite material 30 after curing. Thereby, the fibers of the composite material 30 are neither damaged nor cut for fixing the optical fiber sensors 10 to the composite material 30.

Furthermore, the length direction of the fibers is the length direction of the optical fiber sensors 10. Specifically, the directions of the fibers of the prepreg sheets S1, each laminated at a position lower than each of the top surfaces of the convex portions 3 of the composite material molding jig 1, are one way, and the longitudinal direction of the convex portions 3 is the length direction of the fibers. Therefore, the fibers of the prepreg sheets S1 are not cut for laying the prepreg sheets S1 in both sides of each convex portion 3. Furthermore, the fibers are not interrupted by each convex portion Thereby, deterioration in strengths of the composite material 30 resulting from cutting or damage of the fibers, can be avoided.

When a direction of at least a part of the fibers of the prepreg sheets S2, laminated at positions higher than the top surfaces of the convex portions 3, is made to be a direction intersecting the longitudinal direction of the convex portions 3, strengths in the direction intersecting the longitudinal direction of the convex portions 3 can be secured even when the prepreg sheets S1 in both sides of each convex portion 3 have been separated.

In particular, deterioration in strengths of the composite material 30, resulting from existence of the grooves for fixing the optical fiber sensors 10, is a negligible extent when the number of the prepreg sheet S1 laminated at a position lower than each top surface of the convex portions 3 is made to one sheet by taking advantage of relation that a standard diameter of each optical fiber sensor 10 is approximately same as a standard thickness of one ply of the prepreg sheet S. Therefore, the composite material 30 having necessary strengths can be manufactured easily.

Since each of the optical fiber sensors 10 has a low rigidity, the optical fiber sensors 10 are easily broken by an external force. Therefore, embedding the optical fiber sensors 10 in the composite material 30 is most effective in order to prevent breakage of the optical fiber sensors 10. That is, the optical fiber sensors 10 can be safely shielded by being embedded in the composite material 30.

(Ultrasonic Test System)

Figure 12:
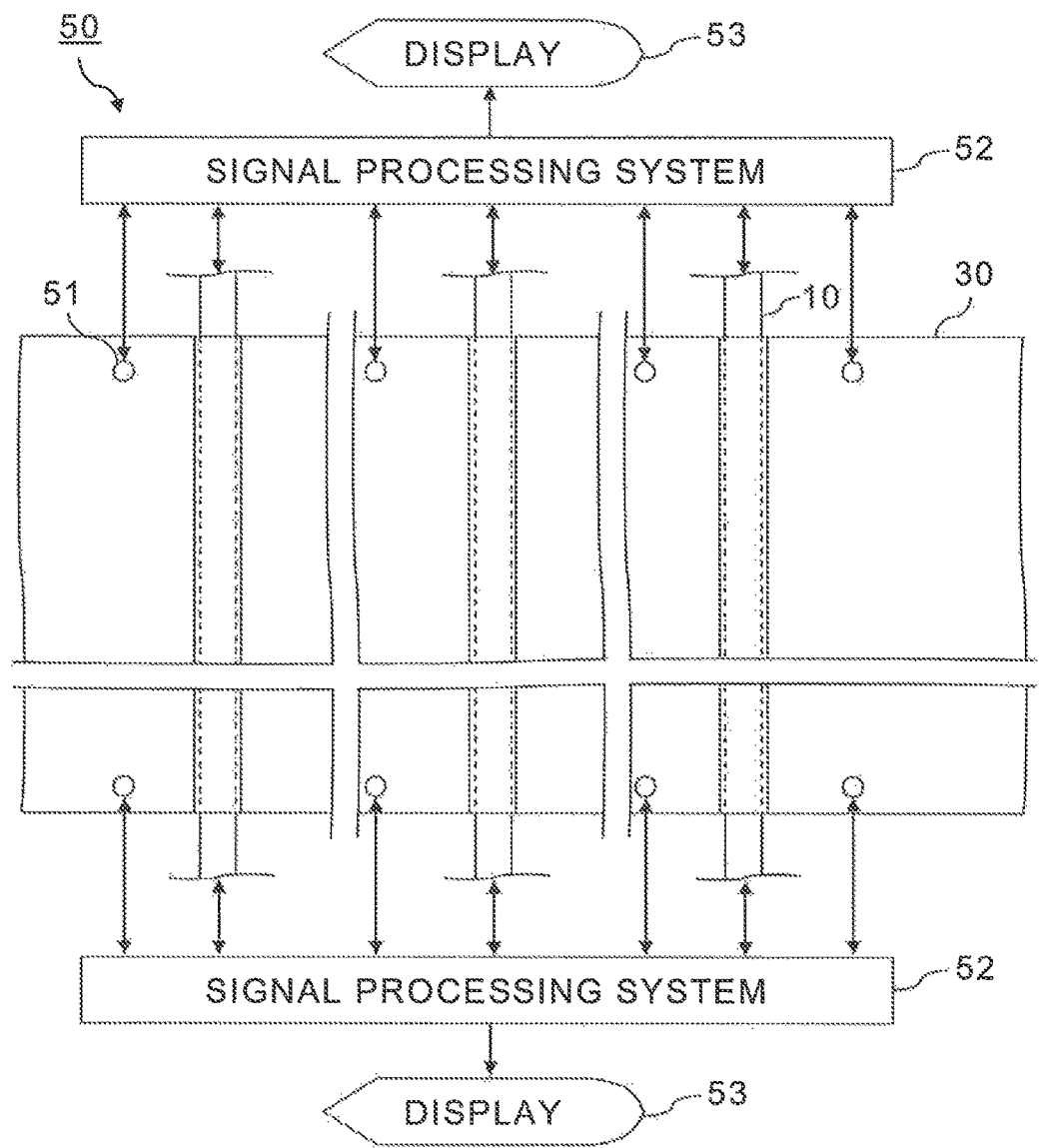
FIG. 12 shows a configuration of an ultrasonic test system including the optical fiber sensors, embedded in the surface of the composite material, as elements.

FIG. 12 shows a configuration of an ultrasonic test system 50 including the optical fiber sensors 10, embedded in the surface of the composite material 30, as elements.

The ultrasonic test system 50 can be composed of actuators 51, the optical fiber sensors 10, embedded in the surface of the composite material 30, and a signal processing system 52. Each of the actuators 51 is an ultrasonic transducer which emits an ultrasonic wave toward a test area of the composite material 30.

As described above, the optical fiber sensors 10 embedded in the surface of the composite material 30 can be manufactured by curing the laminated body 20 of prepregs, which has grooves, to mold the composite material 30, which has the grooves, inserting the optical fiber sensors 10 with an adhesive into the grooves of the composite material 30, and hardening the adhesive. For example, the composite material 30 of which the optical fiber sensors 10 have been embedded in the surface can be manufactured by molding the composite material 30 which has grooves each having a depth and a width of cross section corresponding to the thickness of one ply of the prepreg sheet S, and inserting the optical fiber sensors 10, each having a diameter selected according to the thickness of one ply of the prepreg sheet S, into the grooves respectively.

Each of the optical fiber sensors 10 detects at least one of an ultrasonic wave which has transmitted a test area of an object to be tested made of the composite material 30 and a reflected wave of the ultrasonic wave which has reflected in the test area, to output a detection signal. That is, at least one of an ultrasonic wave which has transmitted a test area and an ultrasonic reflected wave which has reflected in the test area can be used for a flaw detection test of the test area. Therefore, relative positions of the optical fiber sensors 10 and the actuators 51 are determined depending on which of ultrasonic waves which have transmitted the test areas and ultrasonic reflected waves which have reflected in the test areas are to he detected.

As described above, the optical fiber sensors 10 are to be inserted into grooves, which have been formed between uncut fibers of the composite material 30 so that the length direction of the grooves becomes the same direction as the length direction of the fibers before curing. The positions and directions of the grooves for inserting the optical fiber sensors 10 are determined so that at least one of ultrasonic waves which have transmitted test areas of the composite material 30 and ultrasonic reflected waves which have reflected in the test areas can be detected by the optical fiber sensors 10 respectively. An interval of the optical fiber sensors 10 can be 0.5 m depending on detection sensitivity of ultrasonic waves, for example.

Typical examples of the optical fiber sensor 10 include a PS-FBG (phase-shifted FBG) sensor besides an FBG sensor. An FBG sensor detects an ultrasonic wave by detecting a change of light transmission characteristics or light reflection characteristics of an FBG, which vary by a strain change caused by vibration propagating in the test target, as an optical signal. Meanwhile, a PS-FBG is an FBG in which a local phase shift has been introduced in a periodic change of a refractive index. When a PS-FBG sensor is used, detection sensitivity of ultrasonic waves can be dramatically improved, compared to a case where an FBG sensor is used.

Especially preferable ultrasonic waves include a Lamb wave from a viewpoint of improving SNR (signal-to-noise ratio) and accuracy of an optical signal which is obtained by each of the optical fiber sensors 10 as an ultrasonic detection signal. A Lamb wave propagates in a thin plate of which thickness is not more than half of a wavelength of the ultrasonic wave Therefore, it is preferable to transmit Lamb waves from the actuators 51.

The signal processing system 52 has a function to emit ultrasonic waves toward a test area from the actuators 51 by outputting control signals to the actuators 51, and a function to detect a flaw in the test area based on detection signals from the optical fiber sensors 10. The signal processing system 52 can be composed of circuitry, including a photoelectric conversion circuit, an A/D (analog-to-digital) converter, and a computer, besides a control circuit which outputs a control signal to each of the actuators 51, at least one light source which outputs laser lights to the optical fiber sensors 10, and optical elements necessary for processing an optical signal, consisting of a reflected light or a transmitted light, which is output from each of the optical fiber sensors 10 as a detection signal of an ultrasonic wave. Furthermore, the signal processing system 52 has a function to perform signal processing, such as noise removal processing, averaging processing, envelope detection processing, peak detection processing, and threshold processing, necessary for detecting a flaw. A display 53 can be coupled to the signal processing system 52 so that information necessary for a user, such as the existence of a flaw and a position of the flaw, can be displayed.

More specifically, at least a part of elements, which process electric signals and digital information, composing the signal processing system 52 can be implemented by circuitry including at least one semiconductor integrated circuit such as at least one processor (e.g., a central processing unit (CPU)), at least one application specific integrated circuit (ASIC), and/or at least one field programmable gate array (FPGA). At least one processor can be configured, by reading instructions from at least one machine readable tangible medium, to perform all or a part of functions of the signal processing system 52. Such a medium may take many forms, including, but not limited to, any type of magnetic medium such as a hard disk, any type of optical medium such as a CD and a DVD, any type of semiconductor memory (i.e., semiconductor circuit) such as a volatile memory and a non-volatile memory. The volatile memory may include a DRAM and a SRAM, and the nonvolatile memory may include a ROM and a NVRAM. The ASIC is an integrated circuit (1C) customized to perform, and the FPGA is an integrated circuit designed to be configured after manufacturing in order to perform, all or a part of the functions of the modules shown in FIG. 12.

Thus, health of the composite material 30 which is used as a material of an aircraft structural object or the like can be monitored using the ultrasonic test system 50 having such a structure. That is, an ultrasonic test of the composite material 30 can be performed using the optical fiber sensors 10 integrated with an object to be tested.

(Aircraft Structural Object)

Figure 13:
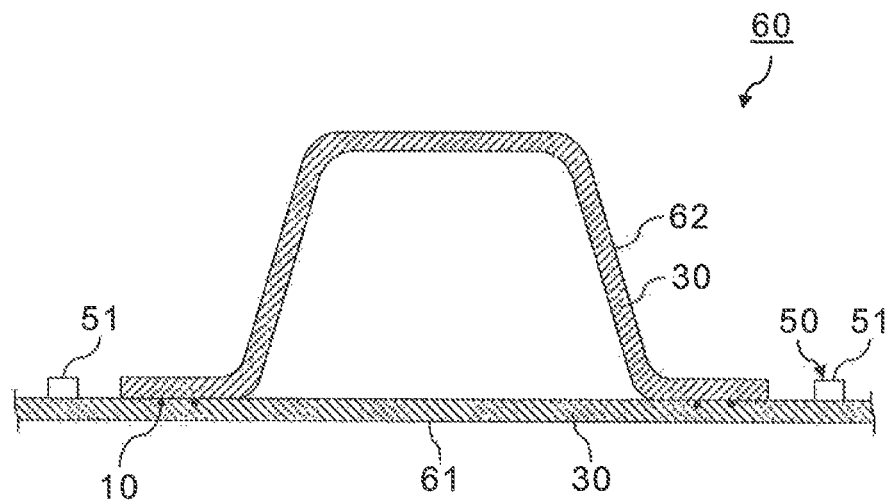
FIG. 13 shows an example of aircraft structural object including the ultrasonic test system, shown in FIG. 12, as a part.

FIG. 13 shows an example of aircraft structural object 60 including the ultrasonic test system 50, shown in FIG. 12, as a part.

Since the optical fiber sensors 10 of the ultrasonic test system 50 are embedded in the composite material 30, the ultrasonic test system 50 can be a part of the aircraft structural object 60, made of the composite material 30. As a specific example, in the case of the aircraft structural object 60 in which a reinforcement member 62, such as a stringer whose cross-section has a hat shape, has been attached to a panel 61 made of the composite material 30, the optical fiber sensors 10 can be embedded between the panel 61 and the reinforcement member 62. As a matter of course, the similar applies to a case where a cross-sectional shape of the reinforcement member 62 is an I shape, a reverse T shape, or the like.

In this case, grooves may be formed on either the panel 61 or the reinforcement member 62 so that the optical fiber sensors 10 can be embedded in the grooves. Alternatively, grooves may be formed on both the panel 61 and the reinforcement member 62 so that the optical fiber sensors 10 can be embedded in the grooves. In the example shown in FIG. 13, a plurality of the optical fiber sensors 10 have been embedded in the panel 61 side so that the longitudinal direction of the reinforcement member 62 becomes the length direction of the optical fiber sensors 10. As a matter of course, a single optical fiber sensor 10 or a plurality of the optical fiber sensors 10 may be embedded so that a direction perpendicular to the longitudinal direction of the reinforcement member 62 becomes the length direction of the single optical fiber sensor 10 or the plural optical fiber sensors 10. In that case, each optical fiber sensor 10 may be disposed not only along the panel 61 side, but also along the reinforcement member 62 side.

Furthermore, the optical fiber sensors 10 may be embedded not only between the panel 61 and the reinforcement member 62, but also between two sheets of the panels 61. That is, the optical fiber sensors 10 can be embedded inside grooves formed in the bonded surface side of at least one of two bonded composite material parts. Therefore, grooves can be formed on at least one of the surfaces to be bonded of the composite material parts, which are objects to be bonded, using the composite material molding jig 1.

As described above, when the optical fiber sensors 10 are embedded between two composite material parts, it becomes possible to easily detect a defect, such as delamination or peeling, at an adhesive part or a bonded part. The aircraft structural object 60, where the optical fiber sensors 10 have been embedded between two composite material parts, can be manufactured in various methods.

In the case of embedding the optical fiber sensors 10 in grooves formed on only one of the two composite material pars, the composite material part on which the grooves have been formed is manufactured by heating and curing one of the composite material parts. Next, the optical fiber sensors 10 are inserted into the grooves, and fixed with an adhesive. Next, a laminated body of prepregs corresponding to the other composite material part is combined with the composite material part, of which the optical fiber sensors 10 have been embedded in the grooves, through an adhesive. Next, the aircraft structural object 60 where the optical fiber sensors 10 have been embedded between the two composite material parts can be manufactured by heating and curing the laminated body of prepregs.

Conversely, in the case of embedding the optical fiber sensors 10 in grooves formed on both composite material parts, the composite material parts on which the grooves have been formed are manufactured by heating and curing the both composite material parts. Next, the composite material parts are combined with each other through an adhesive. At this time, the optical fiber sensors 10 are inserted into the grooves, and fixed with an adhesive. Next, the aircraft structural object 60 where the optical fiber sensors 10 have been embedded between the two composite material parts can be manufactured by hardening the adhesive.

(Second Implementation)

Figure 14:
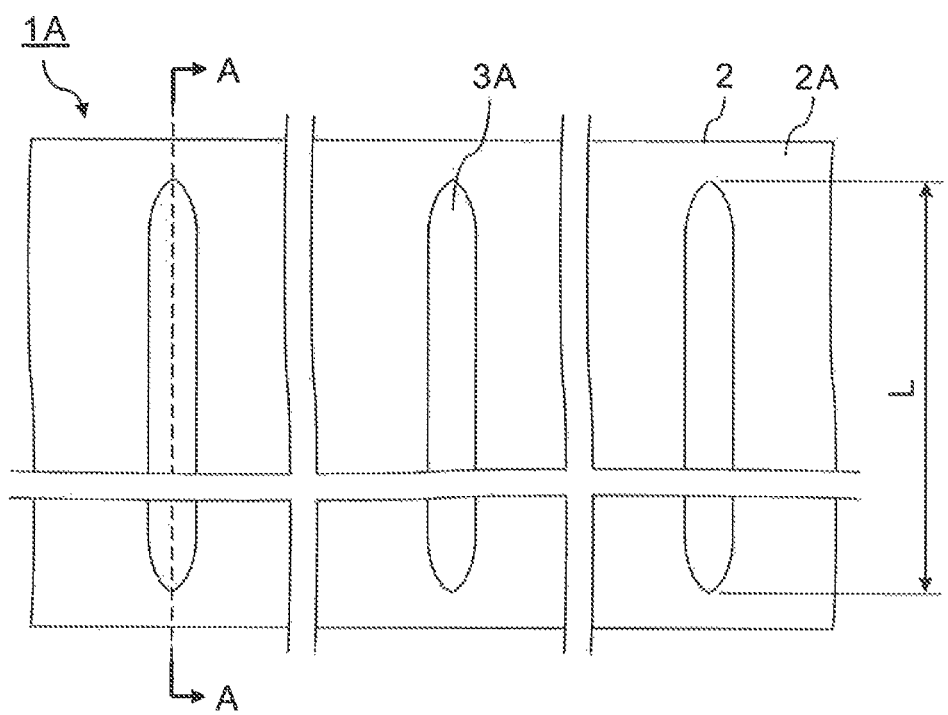
FIG. 14 is a top view showing a structure of a composite material molding jig according to the second implementation of the present invention.
Figure 15:
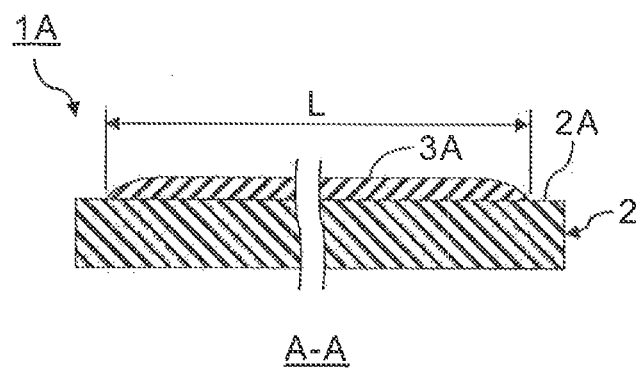
FIG. 15 is.

FIG. 14 is a top view showing a structure of a composite material molding jig according to the second implementation of the present invention. FIG. 15 is a sectional view of the composite material molding jig at the position A-A in FIG. 14.

A composite material molding jig 1A in the second implementation shown in FIG. 14 and FIG. 15 is different from the composite material molding jig 1 in the first implementation in a point that end portions of convex portions 3A are inside end faces of the rigid portion 2. Other structures and functions of the composite material molding jig 1A in the second implementation are not substantially different from those of the composite material molding jig 1 in the first implementation. Therefore, the same structures or corresponding structures are shown by the same signs, and their explanations are omitted.

Each portion of the optical fiber sensors 10, where light transmission characteristics and light reflection characteristics show a peak and which actually functions as a sensor, is about several mm in length. Therefore, in the case of the optical fiber sensor 10 having the length of about 3 m to 5 m, for example, about three to five peaks can be made to appear in light transmission characteristics and light reflection characteristics by giving the optical fiber sensor 10 characteristics in which light transmission characteristics and light reflection characteristics repeat periodically. In many cases of an aircraft structural object, it is appropriate to embed the optical fiber sensors 10, each having the length of about 1 m to 10 m, in the composite material 30.

Thus, each of the convex portions 3A of the composite material molding jig 1A can have a length L of not less than 1 in and not more than 10 m in the longitudinal direction of the convex portions 3A, for example. Thereby, regions which should be tested in most aircraft structural objects can be covered. When the length L of the convex portions 3A in the longitudinal direction is shorter than a distance between the end faces of the rigid portion 2, not through grooves where both ends have not been closed, but blind grooves where both ends or one end has been closed are to be formed on the composite material 30. That is, signal transmission portions of the optical fiber sensors 10 may not be inserted into the grooves of the composite material 30.

In that case, when the optical fiber sensors 10 extremely bend at end portions of the grooves, it may lead to a breakage. Thus, end portions of the grooves can be smoothed so that the optical fiber sensors 10 do not extremely bend at the end portions of the grooves. That is, unevenness can be prevented from being formed at the end portions of the grooves.

As a specific example, at least one of both end portions of each convex portion 3A in the longitudinal direction can have a shape of which the height and the width of cross section gradually decrease as exemplified in FIG. 14 and FIG. 15.

Figure 16:
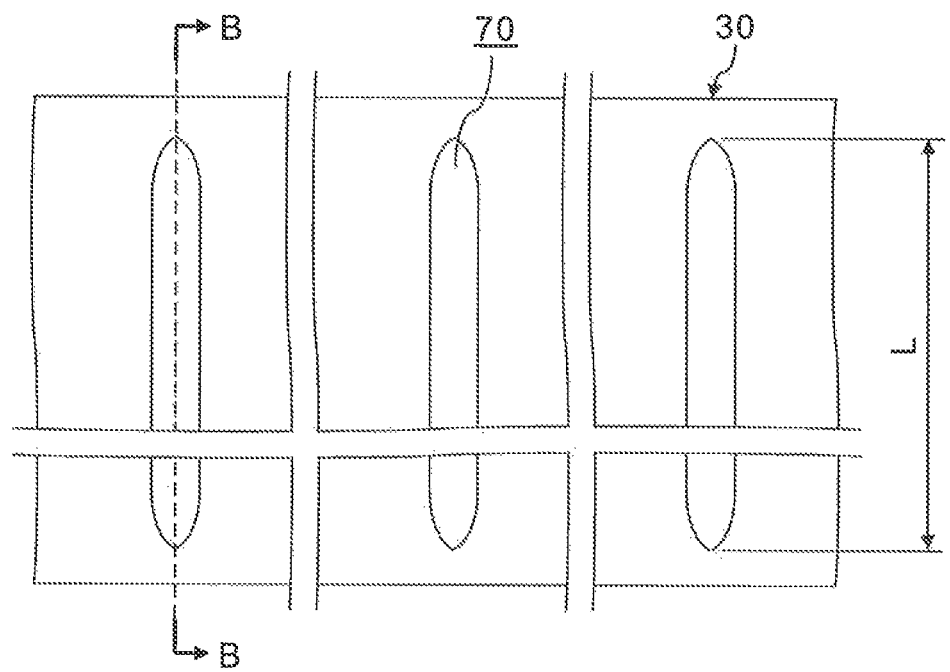
FIG. 16 is a top view showing shapes of grooves of the composite material, formed by the convex portions of the composite material molding jig shown in FIG. 14 and FIG. 15.
Figure 17:
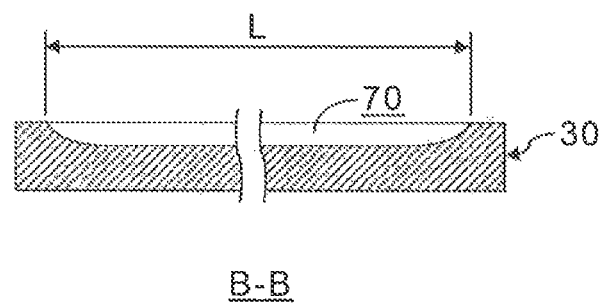
FIG. 17 is a sectional view showing a shape of the groove at the position B-B in FIG. 16.

FIG. 16 is a top view showing shapes of grooves 70 of the composite material 30, formed by the convex portions 3A of the composite material molding jig 1A shown in FIG. 14 and FIG. 15. FIG. 17 is a sectional view showing a shape of the groove 70 at the position B-B in FIG. 16.

When the grooves 70 of the composite material 30 are formed by the convex portions 3A exemplified in FIG. 14 and FIG. 15, at least one of both end portions of each groove 70 in the length direction can have a shape of which the depth and the width of cross section gradually decrease. That is, the composite material 30 having the grooves 70 of which the depth and the width of each cross section of at least one of both end portions gradually decrease can be molded using the composite material molding jig 1A.

In this case, each optical fiber sensor 10 is to be embedded in the blind groove of which both ends or one end has been closed by three dimensionally smooth curved surfaces or a three dimensionally smooth curved surface. Usually, the diameter of an optical fiber for transmitting an optical detection signal from the optical fiber sensor 10 is same as that of the optical fiber sensor 10. That is, the diameter of a sensor portion of an optical fiber is same as that of a signal transmission portion of the optical fiber. Accordingly, only the optical fiber sensor 10 portions can be inserted inside the grooves 70, without extremely bending the optical fibers. Thereby, the optical fiber sensors 10 can be prevented from being bent and damaged.

On the other hand, the end portions of the convex portions 3A also have three dimensionally smooth curved surfaces. Therefore, the prepreg sheets S1 can be disposed along shapes of the convex portions 3A without cutting fibers of prepregs disposed at both sides of each convex portion 3A. Conversely, it is appropriate to determine shapes of the end portions of the convex portions 3A to be smooth enough so that the prepreg sheets S1 can be laid along the convex portions 3A without cutting fibers.

(Other Implementations)

While certain implementations have been described, these implementations have been presented by way of example only, and are not intended to limit the scope of the invention. Indeed, the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms or modifications as would fall within the scope and spirit of the invention.

What is claimed is:

1. A composite material molding method, comprising:
    placing one or more plies of prepreg sheets on a molding jig, the molding jig comprising a rigid portion having a surface for laminating prepreg sheets, and a convex portion for forming a groove for insertion of an optical fiber sensor, the convex portion being formed in a surface side of the rigid portion, and
    heating and curing a laminated body of the prepreg sheets laminated on the molding jig, the groove for inserting the optical fiber sensor having been formed in the one or more prepreg sheets, wherein
    each of the one or more prepreg sheets is, prior to curing, a glass fiber reinforced plastic or a carbon fiber reinforced plastic, and
    placing one or more plies of prepreg sheets on the molding jig comprises disposing one or more plies of prepreg sheets on each of both sides of the convex portion for forming the groove, with a length direction of fibers of the disposed one or more plies of prepreg sheets being a length direction of the convex portion.

2. The composite material molding method according to claim 1,
    wherein the convex portion has a height of one ply of a prepreg sheet.

3. The composite material molding method according to claim 1,
    wherein a height of the convex portion and a width of a cross section of the convex portion are not less than 125 µm and not more than 150 µm, respectively.

4. The composite material molding method according to claim 1,
    wherein the convex portion has a length not more than 10 m in a longitudinal direction of the convex portion.

5. The composite material molding method according to claim 1,
    wherein the groove has a depth corresponding to one ply of a prepreg sheet.

6. The composite material molding method according to claim 1, further comprising:
    inserting an optical fiber sensor into the groove formed in the composite material and applying an adhesive between the groove and the optical fiber sensor; and
    hardening the adhesive to produce a composite material integrated with the optical fiber sensor.

7. The composite material molding method according to claim 1,
    wherein at least one of both end portions of the groove in a length direction is made to have a shape of which a depth and a width of a cross section gradually decrease.

8. A composite material molding method comprising:
    producing a laminated body of prepregs, which has a groove for inserting an optical fiber sensor, each of the prepregs, prior to curing, being a glass fiber reinforced plastic or a carbon fiber reinforced plastic; and
    molding a composite material with the prepregs by curing the laminated body of the prepregs, the prepregs having the groove,
    wherein the groove is formed without cutting fibers of the prepregs, a length direction of the groove being a length direction of the fibers, the groove being formed by disposing one or more plies of prepreg sheets on each of both sides of a convex portion for forming the groove, the convex portion being formed on a surface of a rigid composite material molding jig, a length direction of fibers of the disposed one or more plies of prepreg sheets being a length direction of the convex portion.

9. The composite material molding method according to claim 8,
   wherein the groove has a depth corresponding to one ply of a prepreg sheet.

10. The composite material molding method according to claim 8, further comprising:
    inserting an optical fiber sensor into the groove formed in the composite material and applying an adhesive between the groove and the optical fiber sensor; and
    hardening the adhesive to produce a composite material integrated with the optical fiber sensor.

11. The composite material molding method according to claim 8,
    wherein at least one of both end portions of the groove in a length direction is made to have a shape of which a depth and a width of a cross section gradually decrease.

* * * * *